US012779199B2

(12) United States Patent
Xie et al.

(10) Patent No.: US 12,779,199 B2
(45) Date of Patent: Nov. 3, 2026

(54) BLOOD PUMP AND DRIVING DEVICE THEREOF

(71) Applicant: Shenzhen Core Medical Technology Co., Ltd., Shenzhen (CN)

(72) Inventors: Duanqing Xie, Shenzhen (CN); Shunzhou Yu, Shenzhen (CN)

(73) Assignee: Shenzhen Core Medical Technology Co., Ltd., Shenzhen (CN)

( * ) Notice: Subject to any disclaimer, the term of this patent is extended or adjusted under 35 U.S.C. 154(b) by 538 days.

(21) Appl. No.: 18/281,708

(22) PCT Filed: Nov. 15, 2022

(86) PCT No.: PCT/CN2022/132049

§ 371 (c)(1), (2) Date: Sep. 12, 2023

(87) PCT Pub. No.: WO2023/098471

PCT Pub. Date: Jun. 8, 2023

(65) Prior Publication Data

US 2024/0149045 A1 May 9, 2024

(30) Foreign Application Priority Data

Dec. 3, 2021 (CN) ......................... 202111470871.6

(51) Int. Cl.

*A61M 60/122* (2021.01)
*A61M 60/216* (2021.01)

(Continued)

(52) U.S. Cl.

CPC ........ *A61M 60/122* (2021.01); *A61M 60/216* (2021.01); *A61M 60/416* (2021.01); *A61M 60/419* (2021.01); *A61M 2205/103* (2013.01)

(58) Field of Classification Search

None

See application file for complete search history.

(56) References Cited

U.S. PATENT DOCUMENTS

| | | | |
|---|---|---|---|
| 5,376,114 | A | 12/1994 | Jarvik |
| 5,851,174 | A | 12/1998 | Jarvik et al. |

(Continued)

FOREIGN PATENT DOCUMENTS

| | | | |
|---|---|---|---|
| CN | 102788022 | A | 11/2012 |
| CN | 112107749 | A | 12/2020 |

(Continued)

OTHER PUBLICATIONS

Extended European Search Report including Written Opinion for Application No. 22900276.1 dated Feb. 21, 2025. 15 pages.

(Continued)

*Primary Examiner* — Michael W Kahelin

(74) *Attorney, Agent, or Firm* — Lerner David LLP

(57) ABSTRACT

A blood pump and a driving device thereof are provided. The driving device comprises a driving shell, a rotor, a stator mechanism, and an electric wire; the driving shell is provided with a mounting cavity and an accommodating cavity which are separated from each other; the rotor comprises a rotating shaft and a magnetic assembly, the rotating shaft is capable of rotating relative to the driving shell, and the magnetic assembly is fixedly connected to the rotating shaft; the stator mechanism is accommodated in the mounting cavity, the stator mechanism is capable of generating a rotating magnetic field for driving the magnetic assembly to rotate, and the magnetic assembly is capable of driving the rotating shaft to rotate around the axis of the rotating shaft; the part of the electric wire-located between the magnetic assembly and the driving shell is accommodated in the accommodating cavity.

18 Claims, 15 Drawing Sheets

(51) Int. Cl.
*A61M 60/416* (2021.01)
*A61M 60/419* (2021.01)

(56) References Cited

U.S. PATENT DOCUMENTS

| | | | | |
|---|---|---|---|---|
| 6,176,848 | B1 | 1/2001 | Rau et al. | |
| 2004/0141286 | A1 | 7/2004 | Willmer et al. | |
| 2010/0121438 | A1* | 5/2010 | Jarvik | F04D 29/605 623/3.13 |
| 2010/0268017 | A1 | 10/2010 | Siess | |
| 2015/0091405 | A1 | 4/2015 | Sakamoto et al. | |
| 2018/0169312 | A1* | 6/2018 | Barry | A61M 60/824 |
| 2019/0298902 | A1 | 10/2019 | Siess et al. | |
| 2020/0038568 | A1 | 2/2020 | Higgins et al. | |
| 2021/0015982 | A1* | 1/2021 | Kerkhoffs | A61M 60/829 |
| 2023/0310834 | A1 | 10/2023 | Yu | |

FOREIGN PATENT DOCUMENTS

| | | | |
|---|---|---|---|
| CN | 112472999 | A | 3/2021 |
| CN | 112494803 | A | 3/2021 |
| CN | 112512622 | A | 3/2021 |
| CN | 112587792 | A | 4/2021 |
| CN | 114796845 | A | 7/2022 |
| CN | 114796846 | A | 7/2022 |
| CN | 114796849 | A | 7/2022 |
| EP | 3862035 | A1 | 8/2021 |
| JP | h08504621 | A | 5/1996 |
| JP | h08322194 | A | 12/1996 |
| JP | 2004173489 | A | 6/2004 |
| JP | 201570765 | A | 4/2015 |
| JP | 2023511326 | A | 3/2023 |
| WO | 2023160422 | A1 | 8/2023 |

OTHER PUBLICATIONS

Notice Allowance for Japanese Application No. 2023-561228 dated Jan. 14, 2025. 3 pages.

International Search Report for PCT/CN2022/132049 mailed Feb. 9, 2023. 5 pgs.

* cited by examiner

BLOOD PUMP AND DRIVING DEVICE THEREOF

CROSS-REFERENCE TO RELATED APPLICATIONS

This application is an U.S. national phase application under 35 U.S.C. § 371 based upon international patent application No. PCT/CN2022/132049, filed on Nov. 15, 2022, which itself claims priority to Chinese Patent Application No. 202111470871.6, filed to the Chinese Patent Office on Dec. 3, 2021. The contents of the above identified applications are hereby incorporated herein in their entireties by reference.

TECHNICAL FIELD

The present disclosure relates to the technical field of medical devices, in particular, to a blood pump and a driving device thereof.

BACKGROUND

An intravascular blood pump is a device designed to be inserted percutaneously into a patient's blood vessel and be probed into the patient's heart as a left ventricular assist device or a right ventricular assist device. The intravascular blood pump may also be referred to as an intracardiac blood pump.

A conventional blood pump mainly includes an impeller and a driving device that drives the impeller to rotate. Driven by the driving device, the impeller transports blood from a blood flow inlet of the blood pump to a blood flow outlet. In this process, malfunctioning (such as breakage or falling off) of an electric wire in the driving device affects normal use of the blood pump.

SUMMARY

Accordingly, the present disclosure provides a blood pump and a driving device thereof, which can prevent malfunctioning of an electric wire in the driving device and ensure normal use of the blood pump.

A driving device includes:

- a driving housing provided with a mounting cavity and an accommodating cavity separated from the mounting cavity;
- a rotor comprising a rotating shaft and a magnetic assembly, an end of the rotating shaft being accommodated in the mounting cavity, the rotating shaft being capable of rotating relative to the driving housing, and the magnetic assembly being fixedly connected to the rotating shaft;
- a stator mechanism accommodated in the mounting cavity, the stator mechanism being capable of generating a rotating magnetic field that drives the magnetic assembly to rotate, and the magnetic assembly being capable of driving the rotating shaft to rotate around an axis of the rotating shaft; and
- an electric wire electrically connected to the stator mechanism, a portion of the electrical wire being located between at least part of the magnetic assembly and the driving housing, and the portion of the electric wire located between the magnetic assembly and the driving housing being accommodated in the accommodating cavity, so that a cavity wall of the accommodating cavity prevents the electric wire from being in contact with the magnetic assembly.

A blood bump includes:

- the driving device as described above; and
- an impeller fixedly connected to the rotating shaft, the impeller being capable of rotating along with the rotating shaft.

Details of one or more embodiments of the present disclosure are set forth in the following drawings and descriptions. Other features, objects and advantages of the present disclosure will become apparent from the description, drawings and claims.

BRIEF DESCRIPTION OF THE DRAWINGS

In order to illustrate the embodiments of the present disclosure more clearly, the drawings used in the embodiments will be described briefly. Apparently, the following described drawings are merely for the embodiments of the present disclosure, and other drawings can be derived by those of ordinary skill in the art without any creative effort.

DETAILED DESCRIPTION OF THE EMBODIMENTS

The present disclosure will now be described in detail with reference to the accompanying drawings and embodiments in order to make the objects, technical solutions, and advantages of the present disclosure clearer. It should be understood that the specific embodiments described herein are only for explaining the present disclosure, and not intended to limit the present disclosure.

It should be noted that when an element is referred to as being "fixed to" or "provided on" another element, it may be directly on the other element or may be indirectly on the other element. When an element is referred to as being "connected" to another element, it may be directly connected to the other element or may be indirectly connected to the other element.

In addition, the terms "first" and "second" are only used for descriptive purposes and cannot be understood as indicating or implying relative importance or implicitly indicating the number of indicated technical features. Thus, the features defined with "first" and "second" may explicitly or implicitly include at least one of the features. In the description of the present disclosure, "a plurality of" means two or more than two unless otherwise expressly and specifically defined.

In order to illustrate the technical solution of the present disclosure, the accompanying drawings and embodiments will be described below.

Figure 1:
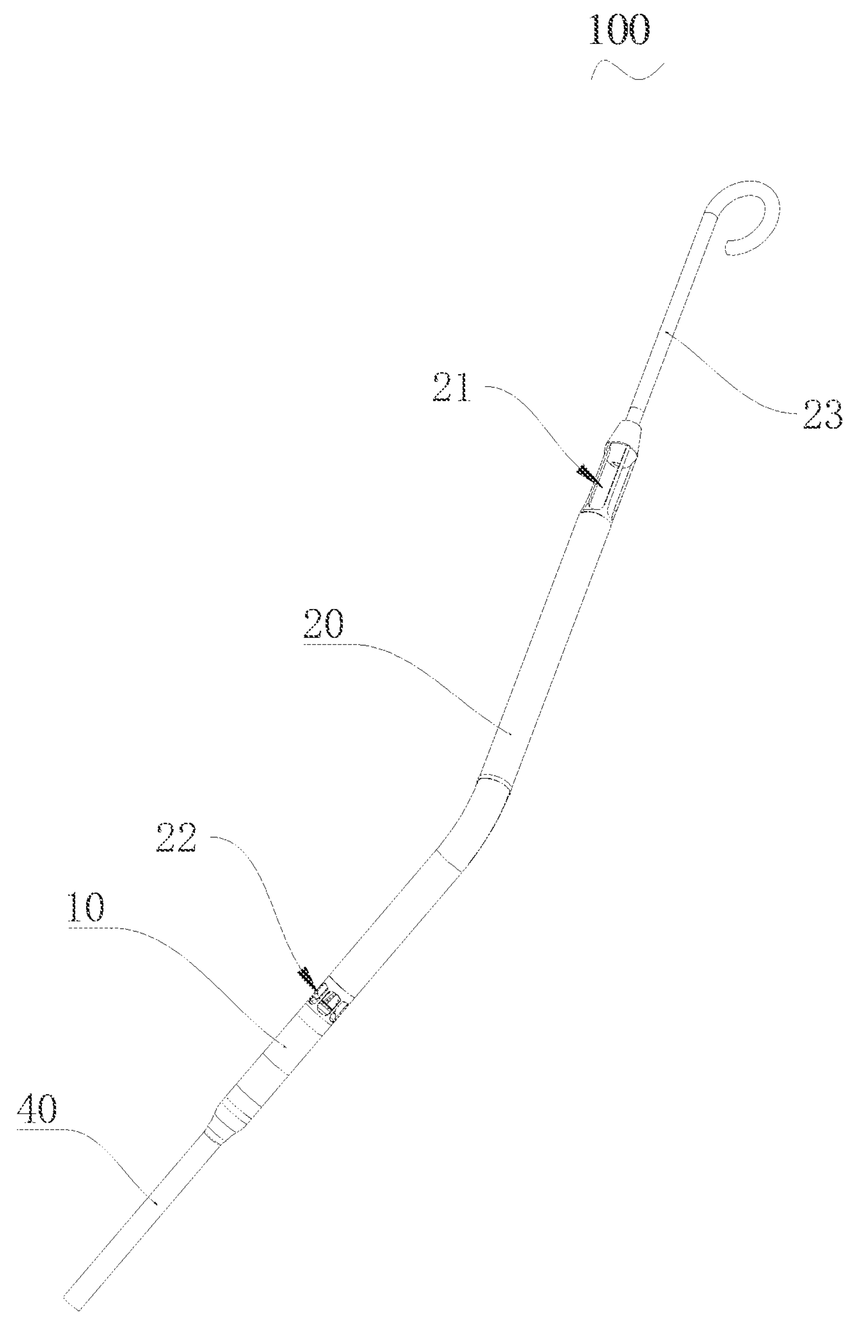
FIG. 1 is a schematic structural view of a blood pump according to an embodiment of the present disclosure.
Figure 2:
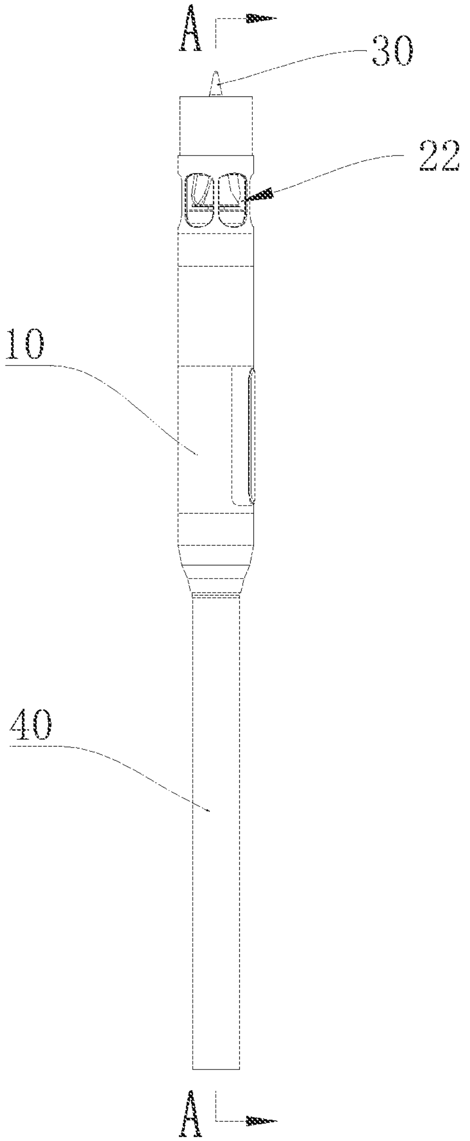
FIG. 2 is a partial schematic structural view of the blood pump shown in FIG. 1.
Figure 3:
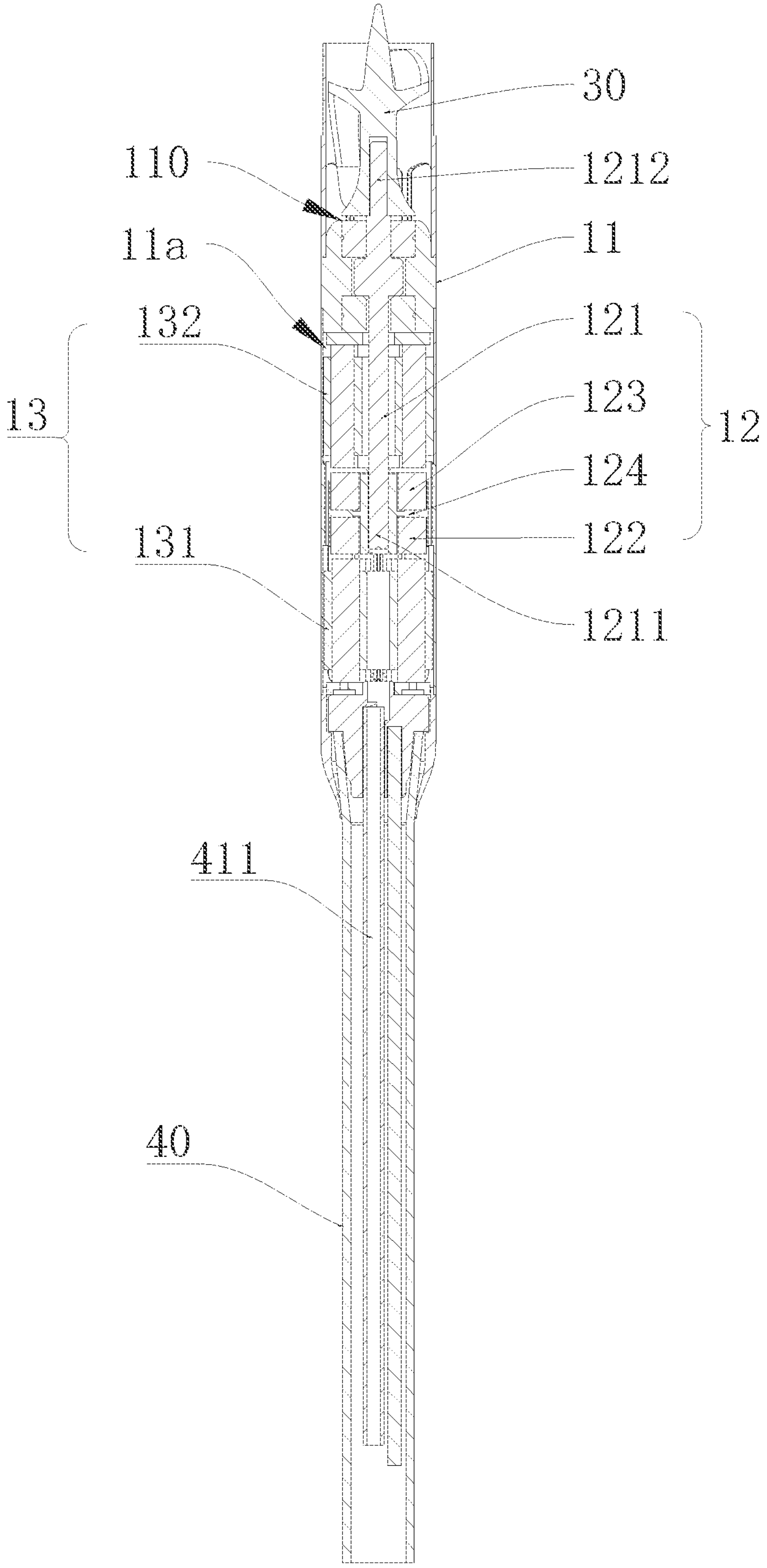
FIG. 3 is a cross-sectional view of the blood pump shown in FIG. 2 taken along the line A-A.

Referring to FIG. 1 to FIG. 3, an embodiment of the present disclosure provides a blood pump 100, including a driving device 10, a cannula assembly 20, and an impeller 30. The cannula assembly 20 is connected to the driving device 10. The impeller 30 is rotatably accommodated in the cannula assembly 20. The impeller 30 is connected to the driving device 10. The driving device 10 can drive the impeller 30 to rotate, so as to implement a blood pumping function of the blood pump 100.

Specifically, the cannula assembly 20 has a flow inlet 21 and a flow outlet 22. In an embodiment, the cannula assembly 20 extends through a heart valve, such as an aortic valve, while the flow inlet 21 is located inside the heart, and the flow outlet 22 and the driving device 10 are located in a blood vessel such as the aorta outside the heart. When the impeller 30 rotates, the blood flows into the cannula assembly 20 from the flow inlet 21 and then flows out of the cannula assembly 20 from the flow outlet 22.

More specifically, an end of the cannula assembly 20 is connected to the driving device 10, the other end of the cannula assembly 20 is provided with a pigtail tube 23. The pigtail tube 23 is configured to stabilize a position of the blood pump 100 in the heart and provide non-invasive support for heart tissues.

Specifically, the pigtail tube 23 has a hollow structure. A material of the pigtail tube 23 is selected from at least one of polyurethane, nylon, polyethylene, polyether block polyamide PEBAX, and latex.

Further, the blood pump 100 further includes a catheter assembly 40. The catheter assembly 40 is connected to the driving device 10, and a supply pipeline is arranged inside the catheter assembly 40. The supply pipeline includes a cleaning pipeline 411 configured to feed cleaning fluid into the driving device 10 and an electrical connecting wire configured to power the driving device 10 and/or to be electrically connected to an external electrical appliance (such as an external controller).

The driving device 10 is in transmission connection with the impeller 30, and the driving device 10 can drive the impeller 30 of the blood pump 100 to rotate. The driving device 10 includes a driving housing 11, a rotor 12, and a stator mechanism 13.

The driving housing 11 is substantially cylindrical. The driving housing 11 is provided with a mounting cavity 11*a*. The impeller 30 is provided outside the driving housing 11. The driving housing 11 is provided with a mounting opening 110 in communication with the mounting cavity 11*a*. The mounting opening 110 is located on a side of the driving housing 11 adjacent to the impeller 30. Specifically, the mounting opening 110 is in communication with the driving housing 11 and the cannula assembly 20. The cleaning fluid fed in the cleaning pipeline 411 can flow through an interior of the driving housing 11 and flow into the cannula assembly 20 from the mounting opening 110, so as to prevent the blood from penetrating into the driving housing 11 from the mounting opening 110 of the driving housing 11.

The rotor 12 is rotatably mounted in the driving housing 11, the rotor 12 is fixedly connected to the impeller 30, and the rotor 12 can drive the impeller 30 to rotate. The rotor 12 includes a rotating shaft 121 and a magnetic assembly, and the magnetic assembly is fixedly connected to the rotating shaft 121. An end of the rotating shaft 121 is accommodated in the mounting cavity 11*a*, the other end of the rotating shaft 121 is located outside the driving housing 11 and fixedly connected to the impeller 30. The rotating shaft 121 can rotate relative to the driving housing 11. Specifically, the rotating shaft 121 rotatably extends through the mounting opening 110. The end of the rotating shaft 121 configured to be connected to the impeller 30 extends from the mounting opening 110 to the outside of the driving housing 11.

Specifically, the rotating shaft 121 is made of a material such as ceramics or stainless steel, for example, alumina toughened zirconia (ATZ), SUS316L, or the like, so as to prevent breakage of the rotating shaft 121.

The stator mechanism 13 is accommodated in the mounting cavity 11*a*, and the stator mechanism 13 can drive the rotor 12 to rotate. Specifically, the stator mechanism 13 can generate a rotating magnetic field for driving the magnetic assembly to rotate, and the magnetic assembly can drive the rotating shaft 121 to rotate around an axis of the rotating shaft 121. The stator mechanism 13 includes a driving stator 131. The driving stator 131 and the rotating shaft 121 are provided spaced apart along the axis of the rotating shaft 121. That is, the rotating shaft 121 does not extend into the driving stator 131. The magnetic assembly includes a first magnet 122, and the first magnet 122 is fixedly connected to the rotating shaft 121. The driving stator 131 can generate a rotating magnetic field interacting with the first magnet 122, so that the first magnet 122 can drive the rotating shaft 121 to rotate around the axis of the rotating shaft 121, thereby driving the impeller 30 to rotate.

Figure 4:
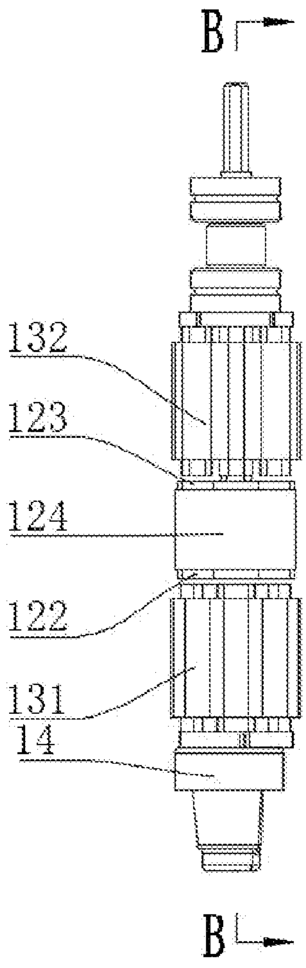
FIG. 4 is a schematic structural view of a driving device of the blood pump shown in FIG. 2 after removing a driving housing.
Figure 5:
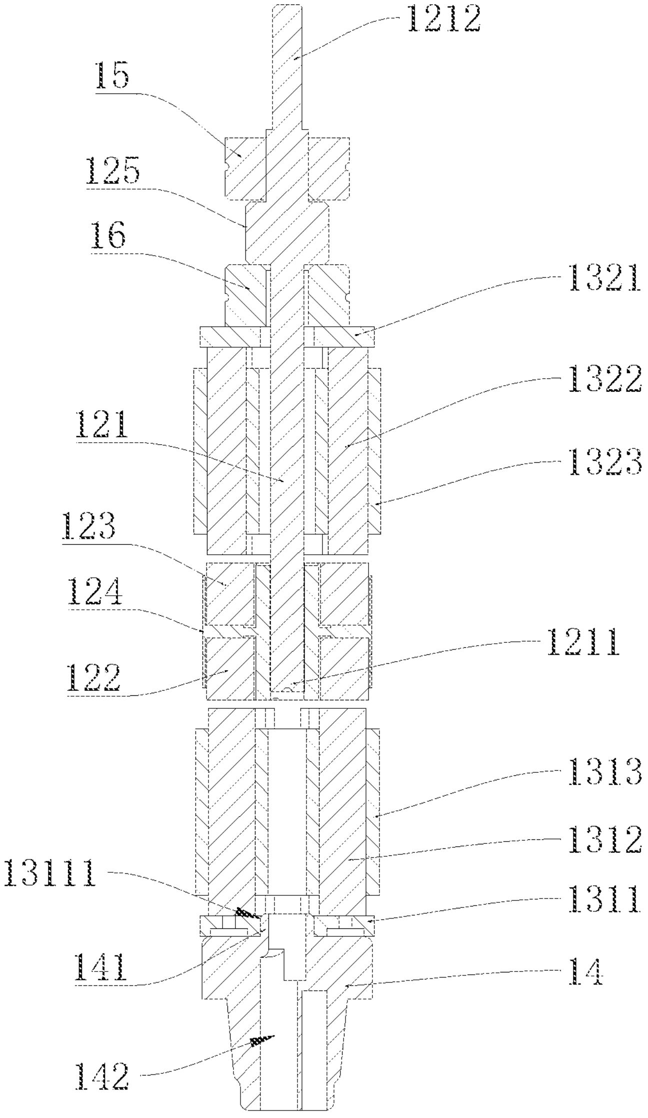
FIG. 5 is a cross-sectional view of the driving device shown in FIG. 4 taken along the line B-B.

Referring to FIG. 4 and FIG. 5, specifically, the driving stator 131 includes a first back plate 1311, a plurality of first magnetic cores 1312, and a plurality of first coils 1313 surrounding the plurality of first magnetic cores 1312. The first back plate 1311 is fixedly connected in the driving housing 11. The plurality of first magnetic cores 1312 are provided spaced apart for one circle around the axis of the rotating shaft 121. Specifically, an extension direction of each first magnetic core 1312 is parallel to that of the rotating shaft 121. An end of each first magnetic core 1312 is fixedly connected to the first back plate 1311, the other end of each first magnetic core 1312 extends to be adjacent to the first magnet 122. The first coil 1313 can generate a rotating magnetic field interacting with the first magnet 122, thereby causing the first magnet 122 to rotate, so as to drive the rotating shaft 121 to rotate, and the impeller 30 rotates along with the rotating shaft 121.

It should be noted that, in some embodiments, the driving stator 131 may not be provided with the first back plate 1311. The first back plate 1311 acts as a closed magnetic circuit, so as to promote and increase generation of magnetic flux of the driving stator 131 and improve a coupling capability. Since the first back plate 1311 can increase the magnetic flux, the arrangement of the first back plate 1311 facilitates reducing an overall diameter of the blood pump 100. The first back plate 1311 and the first magnetic core 1312 are made of a same material. In some embodiments, both the first back plate 1311 and the first magnetic core 1312 are made of soft magnetic materials, such as cobalt steel.

In this embodiment, the driving device 10 further includes a fixing member 14 fixed in the driving housing 11. The fixing member 14 is provided with a positioning post 141. The first back plate 1311 is provided with a positioning hole 13111, and the positioning post 141 extend into the positioning hole 13111, so as to facilitate positioning and mounting of the driving stator 131. An axis of the positioning post 141 coincides with that of the rotating shaft 121.

Specifically, the fixing member 14 is provided with a through hole 142 in communication with an inner cavity of the driving housing 11. The through hole 142 is configured to accommodate an end of the cleaning pipeline 411 adjacent to the impeller 30.

Further, the magnetic assembly further includes a second magnet 123, and the second magnet 123 is fixedly connected to the rotating shaft 121. The stator mechanism 13 further includes a power stator 132. The power stator 132 and the driving stator 131 are provided along the axis of the rotating shaft 121, and the power stator 132 is closer to the impeller 30 than the driving stator 131. That is, in the extension direction of the rotating shaft 121, the power stator 132 is arranged between the impeller 30 and the driving stator 131. The rotating shaft 121 rotatably extends through the power stator 132, and the power stator 132 can generate a rotating magnetic field for driving the second magnet 123 to rotate. The driving stator 131 and the power stator 132 can respectively drive the first magnet 122 and the second magnet 123 to rotate, so that the driving stator 131 and the power stator 132 can cooperatively drive the rotating shaft 121 to rotate around the axis of the rotating shaft 121, thereby driving the impeller 30 to rotate, so as to provide a greater driving force for the rotation of the impeller 30.

In the illustrated embodiment, the first magnet 122 and the second magnet 123 are arranged between the driving stator 131 and the power stator 132. Specifically, the magnetic assembly further includes a flywheel 124 fixedly connected to the rotating shaft 121, the flywheel 124 is located between the power stator 132 and the driving stator 131, and the first magnet 122 and the second magnet 123 are both provided on the flywheel 124.

Specifically, referring to FIG. 2 and FIG. 3, an end of the rotating shaft 121 away from the impeller 30 is referred to as a first end 1211, and an end of the rotating shaft 121 adjacent to the impeller 30 is referred to as a second end 1212. The flywheel 124 fixedly sleeved on the first end 1211 of the rotating shaft 121. The flywheel 124 may be integrally formed with the rotating shaft 121, or may be fixed to the rotating shaft 121 by means of bonding, welding, or the like.

Through the arrangement of the flywheel 124, connection strength between the magnet and the rotating shaft 121 can be improved, and stability of the rotation of the rotating shaft 121 can be improved. In addition, by arranging both the first magnet 122 and the second magnet 123 on the same flywheel 124, the shaking of the rotating shaft 121 during the rotation can be reduced, so that the rotating shaft 121 is more stable during the rotation.

Figure 6:
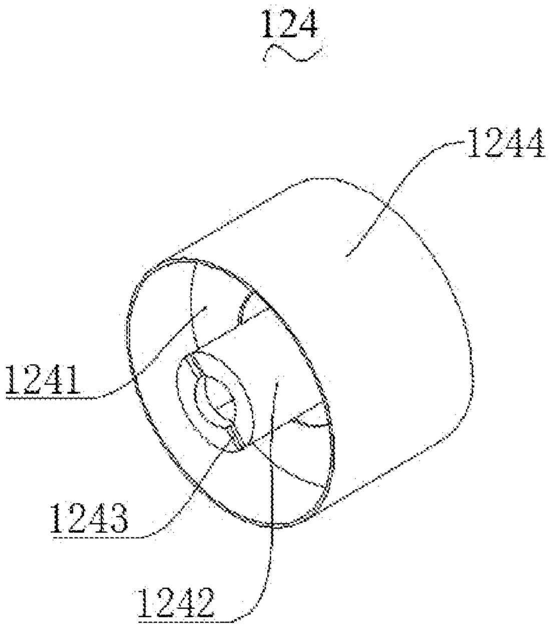
FIG. 6 is a perspective view of a flywheel of the driving device shown in FIG. 4.
Figure 7:
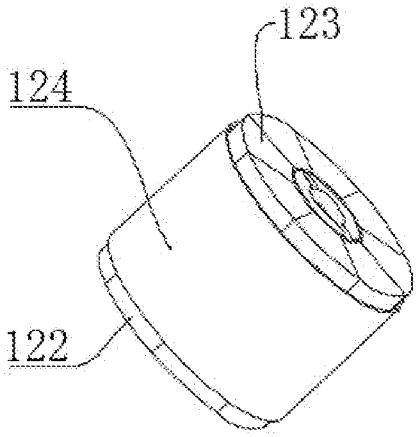
FIG. 7 is a perspective assembly view of a flywheel, a first magnet, and a second magnet of the driving device shown in FIG. 4.
Figure 8:
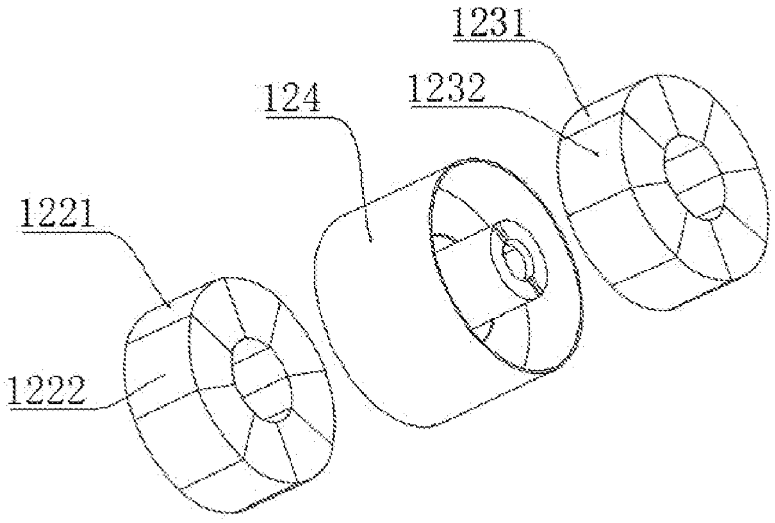
FIG. 8 is an exploded view of the flywheel, the first magnet, and the second magnet shown in FIG. 7.
Figure 9:
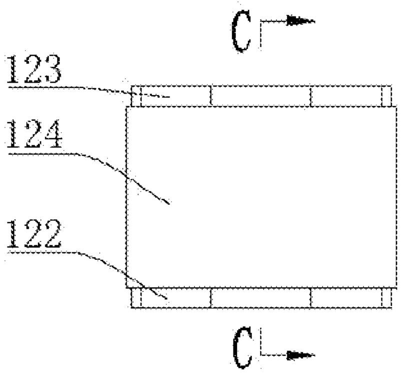
FIG. 9 is a front view of the flywheel, the first magnet, and the second magnet shown in FIG. 7.
Figure 10:
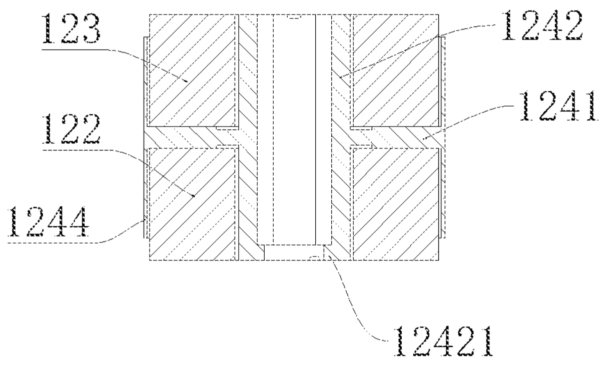
FIG. 10 is a cross-sectional view of the flywheel, the first magnet, and the second magnet shown in FIG. 9 taken along the line C-C.

More specifically, referring to FIG. 6, the flywheel 124 includes a disc-shaped portion 1241 and a tubular portion 1242. The tubular portion 1242 is fixedly extends through a middle portion of the disc-shaped portion 1241 and is coaxial with the disc-shaped portion 1241, the end of the rotating shaft 121 (i.e., the first end 1211) away from the impeller 30 is fixedly accommodated in the tubular portion 1242. The first magnet 122 and the second magnet 123 are provided on two opposite sides of the disc-shaped portion 1241, respectively, so as to facilitate assembly of the first magnet 122 and the second magnet 123 to better fix the first magnet 122 and the second magnet to the rotating shaft 121.

Referring to FIG. 7 to FIG. 10, specifically, both the first magnet 122 and the second magnet 123 are annular Halbach array magnets. The first magnet 122 includes a plurality of first magnetic blocks 1221 whose magnetization directions are parallel to an axis of the first magnet 122. The second magnet 123 includes a plurality of second magnetic blocks 1231 whose magnetization directions are parallel to an axis of the second magnet 123. The plurality of second magnetic blocks 1231 and the plurality of first magnetic blocks 1221 are provided on two opposite sides of the disc-shaped portion 1241 around the rotating shaft 121, respectively. In the extension direction of the rotating shaft 121, each second magnetic block 1231 is opposite to one first magnetic block 1221, and polarities of the second magnetic block 1231 and the first magnetic block 1221 arranged oppositely on a side of the disc-shaped portion 1241 are opposite. Such arrangement can facilitate mounting of the first magnet 122 and the second magnet 123, and prevent difficult assembly caused by mutual repulsion between the magnetic blocks of the first magnet 122 and the magnetic blocks of the second magnet 123.

In some embodiments, the first magnet 122 further includes a plurality of third magnetic blocks 1222 magnetized along a circumferential direction of the first magnet 122. The third magnetic blocks 1222 magnetized in the circumferential direction and the first magnetic blocks 1221 magnetized along a direction parallel to the axis of the first magnet 122 are provided alternately along a circumference of the first magnet 122. Magnetization directions of adjacent first magnetic blocks 1221 are opposite. For example, the magnetization direction of one of the adjacent first magnetic blocks 122 is from a side of the first magnet block 1221 away from the disc-shaped portion 1241 to a side of the first magnet block 1221 facing the disc-shaped portion 1241, and the magnetization direction of the other of the adjacent first magnetic blocks 122 is from the side of the first magnetic block 1221 facing the disc-shaped portion 1241 to the side of the first magnetic block 1221 away from the disc-shaped portion 1241. Magnetization directions of adjacent third magnetic blocks 1222 are opposite on the circumference of the first magnet 122.

Correspondingly, the second magnet 123 further includes a plurality of fourth magnetic blocks 1232 magnetized along a circumferential direction of the second magnet 123. The fourth magnetic blocks 1232 and the second magnetic blocks 1231 are provided alternately along a circumference of the second magnet 123. Magnetization directions of adjacent second magnetic blocks 1231 are opposite, and magnetization directions of adjacent fourth magnetic blocks 1232 are opposite on the circumference of the second magnet 123.

It should be noted that the magnetization directions of the third magnetic block 1222 and the fourth magnetic block 1232 are not limited to circumferential magnetization. In some embodiments, the magnetization directions of the third magnetic block 1222 and the fourth magnetic block 1232 may alternatively be inclined relative to the axis of the rotating shaft 121.

In this embodiment, the first magnet 122 and the second magnet 123 are each provided with eight magnetic blocks. That is, four first magnetic blocks 1221, four second magnetic blocks 1231, four third magnetic blocks 1222, and four fourth magnetic blocks 1232 are provided. The first magnetic block 1221, the second magnetic block 1231, the third magnetic block 1222, and the fourth magnetic block 1232 are all fan-ring magnets, and the first magnet 122 and the second magnet 123 are substantially ring-shaped. It should be understood that, in other embodiments, the first magnet 122 and the second magnet 123 may alternatively be composed of more or fewer magnetic blocks, such as two, four, six, or ten.

In order to facilitate the mounting of the first magnet 122 and the second magnet 123, the flywheel 124 is further provided with an identification portion 1243 for determining mounting positions of the first magnetic blocks 1221 and mounting positions of the second magnetic blocks 1231. The identification portion 1243 may be configured as a groove, a scale line, or a logo. When the first magnetic block 1221 and the second magnetic block 1231 are mounted, as long as the positions of one of the first magnetic blocks 1221 and one of the second magnetic blocks 1231 are identified by the identification portion 1243, the mounting positions of the remaining magnetic blocks can be determined, thereby facilitating the mounting of the first magnet 122 and the second magnet 123. Specifically, the identification portion 1243 may be provided on at least one of the tubular portion 1242 and the disc-shaped portion 1241.

Figure 11:
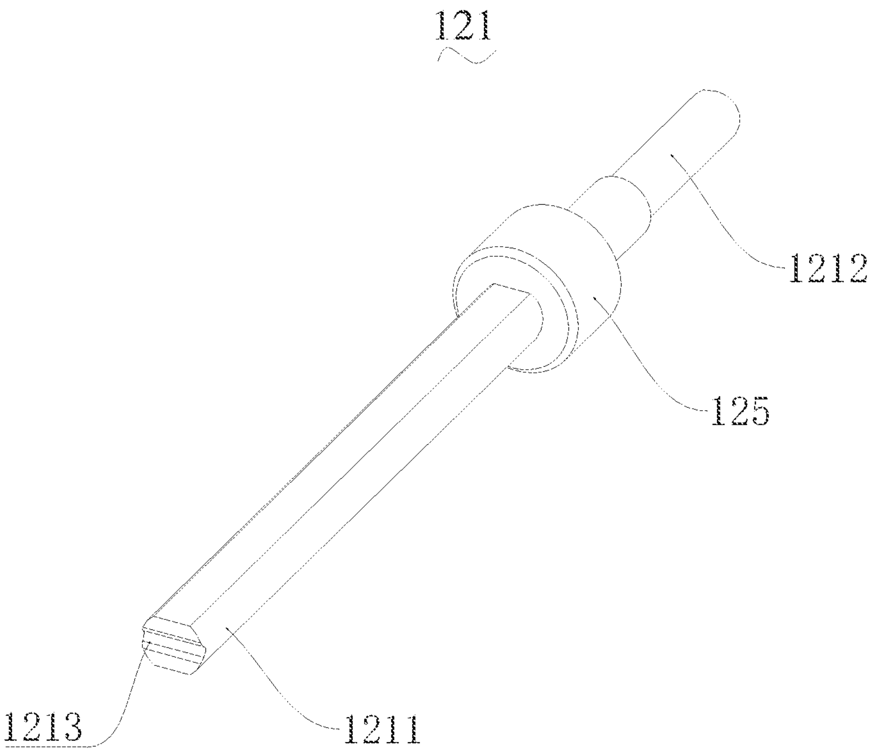
FIG. 11 is a schematic structural view of a rotating shaft shown in FIG. 3.

In one of the embodiments, the flywheel 124 is fixed to the rotating shaft 121 by bonding. Referring to FIG. 11, an end portion of the first end 1211 of the rotating shaft 121 is provided with a dispensing groove 1213, and an inner wall of the tubular portion 1242 is provided with a stop protrusion 12421 abutting against the dispensing groove 1213. In this way, glue can be arranged in the dispensing groove 1213 to facilitate a fixed connection of the rotating shaft 121 and the stop protrusion 12421.

Further, the dispensing groove 1213 extends along a direction perpendicular to the axis of the rotating shaft 121, and an end portion of the dispensing groove 1213 extends to an outer peripheral surface of the rotating shaft 121. Through such arrangement, the glue can be arranged in the dispensing groove 1213, and the glue overflows to the outer peripheral surface of the rotating shaft 121 to bond an inner peripheral wall of the tubular portion 1242 and a peripheral surface of the rotating shaft 121, so that the rotating shaft 121 and the flywheel 124 can be better fixed, or it is also convenient for excess glue used for bonding the rotating shaft 121 and the tubular portion 1242 to overflow into the dispensing groove 1213.

Referring to FIG. 6 to FIG. 10, in this embodiment, the flywheel 124 further includes an outer ring wall 1244 surrounding the disc-shaped portion 1241. The outer ring wall 1244, the tubular portion 1242, and the disc-shaped portion 1241 cooperatively define a first accommodating portion and a second accommodating portion that are configured to accommodate the first magnet 122 and the second magnet 123, respectively, and the first accommodating portion and the second accommodating portion are separated by the disc-shaped portion 1241. Such arrangement can limit the position of the first magnet 122 and the second magnet 123, which not only facilitates the mounting of the first magnet 122 and the second magnet 123, but also enable the bonding of the first magnet 122 and the second magnet 123 to the flywheel 124 to be more stable.

In this embodiment, in an axial direction of the tubular portion 1242, a side of the first magnet 122 away from the disc-shaped portion 1241 is higher than the outer ring wall 1244 by a distance, and a side of the second magnet 123 away from the disc-shaped portion 1241 is higher than the outer ring wall 1244 by a distance, so as to facilitate assembling the first magnet 122 and the second magnet 123 on the flywheel 124.

It should be noted that the flywheel 124 is not limited to the above structure. In some embodiments, the flywheel 124 is not provided with the outer ring wall 1244. In some embodiments, the flywheel 124 is not provided with the outer ring wall 1244 and the tubular portion 1242. In this case, the rotating shaft 121 fixedly extends through the disc-shaped portion 1241, for example, fixedly extends through a center of the disc-shaped portion 1241. Compared with the flywheel 124 provided only with the disc-shaped portion 1241, the arrangement of the tubular portion 1242 enables the flywheel 124 to be more stably connected to the rotating shaft 121.

A structure of the power stator 132 is similar to that of the driving stator 131. The power stator 132 includes a second back plate 1321, a plurality of second magnetic cores 1322, and a plurality of second coils 1323. The plurality of second magnetic cores 1322 are provided spaced apart for one circle around the rotating shaft 121, and an extension direction of each second magnetic core 1322 is parallel to the axis of the rotating shaft 121. An end of each second magnetic core 1322 is fixedly connected to the second back plate 1321, and the other end of each second magnetic core 1322 extends to be adjacent to the second magnet 123. In other words, in the axial direction of the rotating shaft 121, the driving stator 131 and the power stator 132 are oppositely arranged. Each second coil 1323 is wound around the corresponding second magnetic core 1322. The second coil 1323 can generate a rotating magnetic field interacting with the second magnet 123.

The first magnetic core 1312 and the second magnetic core 1322 each include a magnetic post, the first coil 1313 is wound around the magnetic post of the first magnetic core 1312, and the second coil 1323 is wound around the magnetic post of the second magnetic core 1322. A cross-sectional area of the magnetic post of the first magnetic core 1312 is greater than that of the magnetic post of the second magnetic core 1322.

A larger cross-sectional area of the magnetic post indicates greater magnetic flux generated and greater torque of the stator to the magnet, and a required current is low, which is beneficial to reduce power consumption and heat generation. Since the rotating shaft 121 extends through a middle portion of the power stator 132, the cross-sectional area of the second magnetic core 1322 is limited due to a limitation of a radial dimension of the blood pump 100, while the rotating shaft 121 does not extend through a middle portion of the driving stator 131, so that the first magnetic core 1312 can select a larger cross-sectional area. In other words, such arrangement can reduce power consumption and reduce heat generation of the driving device 10.

Figure 12:
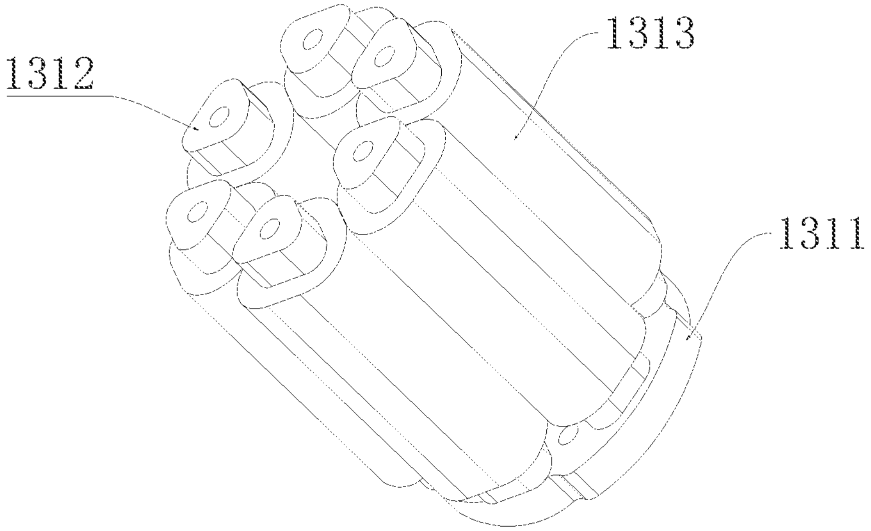
FIG. 12 is a schematic structural view of a driving stator of the driving device shown in FIG. 4.
Figure 13:
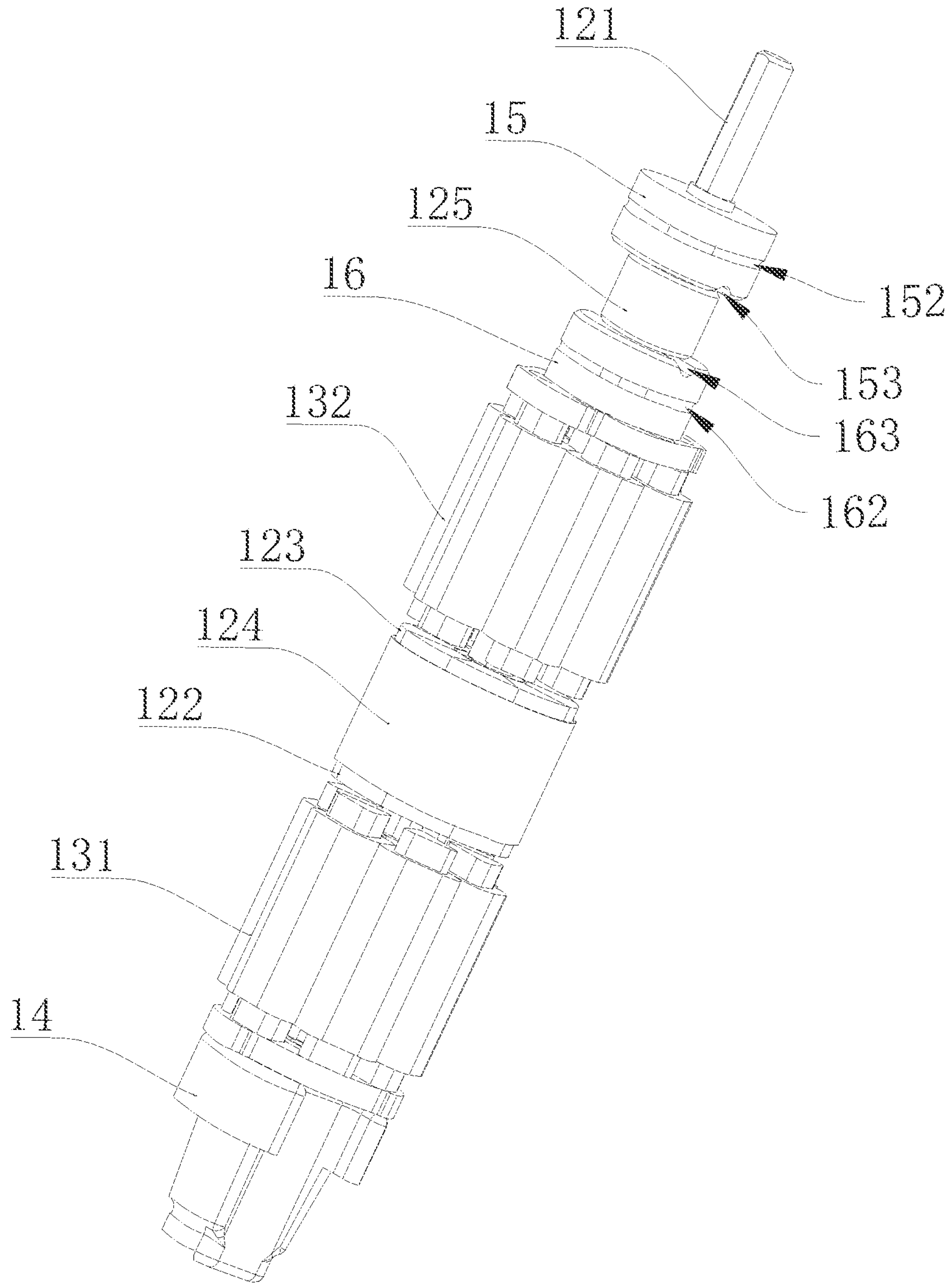
FIG. 13 is a schematic structural view of the driving device shown in FIG. 4 from another perspective after removing the driving housing.

As shown in FIG. 12 and FIG. 13, in this embodiment, both the first magnetic core 1312 and the second magnetic core 1322 are provided only with the magnetic posts. That is, neither the first magnetic core 1312 nor the second magnetic core 1322 has a head (i.e., a pole piece) with a greater width. In a length direction of the first magnetic core 1312 and the second magnetic core 1322, the width thereof is constant. The entire first magnetic core 1312 can be magnetically coupled with the first magnet 122, and the entire second magnetic core 1322 can be magnetically coupled with the second magnet 123. Compared with the magnetic cores provided with pole pieces, the present disclosure can reduce a magnetic loss and increase magnetic coupling density between the first magnetic core 1312 and the first magnet 122 and between the second magnetic core 1322 and the second magnet 123, so as to increase torque of the driving stator 131 to the first magnet 122 (in a case of equal currents) and torque of the power stator 132 to the second magnet 123 (in a case of equal currents). In addition, the first magnetic core 1312 and the second magnetic core 1322 without heads can also greatly reduce a problem of motor power reduction caused by a local magnetic short circuit due to contact between adjacent magnetic cores.

Cross sections of the first magnetic core 1312 and the second magnetic core 1322 each provided only with the magnetic post may be in the shape of fans, circles, trapezoids, fan-rings, or the like. In the illustrated embodiment, the first magnetic core 1312 and the second magnetic core 1322 each provided only with the magnetic post are substantially in the shape of triangular prism, and an edge of each magnetic core faces the axis of the rotating shaft 121. In this embodiment, edges of the first magnetic core 1312 and the second magnetic core 1322 are rounded. The rounding of the edges can facilitate subsequent winding of the coils, and at the same time help to protect insulating materials covering the coils.

It should be understood that, in other embodiments, the first magnetic core 1312 and the second magnetic core 1322 each may further include a head portion provided at an end of the magnetic post, and the first back plate 1311 is connected to an end of the magnetic post of the first magnetic core 1312 away from the head portion. The second back plate 1321 is connected to an end of the magnetic post of the second magnetic core 1322 away from the head portion. Alternatively, in some embodiments, one of the first magnetic core 1312 and the second magnetic core 1322 may be provided with both the magnetic post and the head portion, and the other of the first magnetic core 1312 and the second magnetic core 1322 may be provided only with the magnetic post.

Referring to FIG. 3, FIG. 5, and FIG. 13, the driving device 10 further includes a first shaft sleeve 15, the first shaft sleeve 15 is accommodated in the mounting cavity 11*a*, the first shaft sleeve 15 is fixedly connected to the driving housing 11, and the rotating shaft 121 rotatably extends through the first shaft sleeve 15. A gap is formed between the rotating shaft 121 and the first shaft sleeve 15. By providing the first shaft sleeve 15, a size requirement for assembly of the rotating shaft 121 and the driving housing 11 can be reduced, and rotational friction of the rotating shaft 121 can be reduced at the same time. In order to facilitate the fixed mounting of the first shaft sleeve 15 in the driving housing 11, a first glue groove 152 is arranged on an outer peripheral surface of the first shaft sleeve 15.

In this embodiment, the first shaft sleeve 15 is provided at the mounting opening 110, and the gap between the first shaft sleeve 15 and the rotating shaft 121 is less than or equal to 2 μm. Since it is difficult for smallest red blood cells (about 8 μm in diameter and about 2 μm in thickness) to enter the gap with a width less than or equal to 2 μm, and the backwashing cleaning fluid flows through the gap, the blood is prevented from entering an interior of the driving housing 11 through the communication opening 110.

Specifically, the cleaning fluid may be, for example, physiological saline, heparin-containing physiological saline, glucose, or the like.

In order to prevent pollution of the cleaning fluid and/or corrosion of elements in the driving device 10, both the driving stator 131 and the power stator 132 of the driving device 10 are covered with a waterproof sealing film. The waterproof sealing film may be made of silica gel, glue, or the like.

The driving device 10 further includes a second shaft sleeve 16, the second shaft sleeve 16 is accommodated in the mounting cavity 11*a*, and the second shaft sleeve 16 is fixedly connected to the driving housing 11. The rotating shaft 121 interstitially extends through the second shaft sleeve 16, and the rotating shaft 121 can rotate in the second shaft sleeve 16. The second shaft sleeve 16 and the first shaft sleeve 15 are provided spaced apart along the extension direction of the rotating shaft 121, and the first shaft sleeve 15 is closer to the impeller 30 than the second shaft sleeve 16. Addition of the second shaft sleeve 16 on the basis of the first shaft sleeve 15 can improve stability of the rotation of the rotating shaft 121.

In order to facilitate the fixed mounting of the second shaft sleeve 16 in the driving housing 11, an outer circumferential surface of the second shaft sleeve 16 is provided with a second glue groove 162. The arrangement of the second glue groove 162 can facilitate bonding of the second shaft sleeve 16 to the driving housing 11 by providing the adhesive in the first glue groove 152.

Specifically, the first shaft sleeve 15 and the second shaft sleeve 16 are made of a metal material, a ceramic material, or the like.

Referring to FIG. 3, FIG. 5, and FIG. 13, in this embodiment, the rotor 12 further includes a limiting ring 125, and the limiting ring 125 is fixedly sleeved on the rotating shaft 121. The limiting ring 125 may be integrally formed with the rotating shaft 121, or may be fixed to the rotating shaft 121 by bonding, welding, or the like. The limiting ring 125 is located between the first shaft sleeve 15 and the second shaft sleeve 16. An outer diameter of the limiting ring 125 is greater than an inner diameter of the first shaft sleeve 15. At the same time, the outer diameter of the limiting ring 125 is also greater than an inner diameter of the second shaft sleeve 16, so as to limit the rotating shaft 121 in the extension direction of the rotating shaft 121 and prevent significant movement of the rotating shaft 121 relative to the driving housing 11 in the extension direction of the rotating shaft 121.

Figure 14:
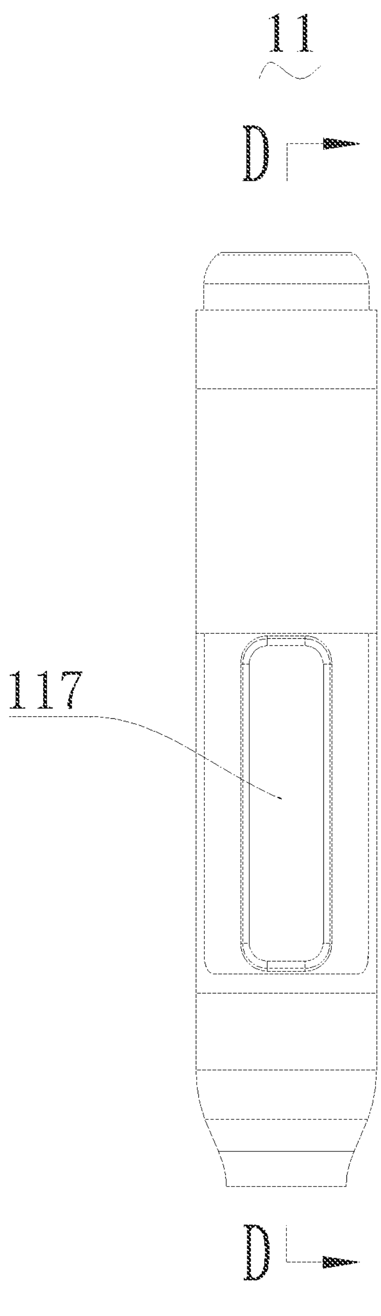
FIG. 14 is a schematic structural view of the driving housing of the blood pump shown in FIG. 1.
Figure 15:
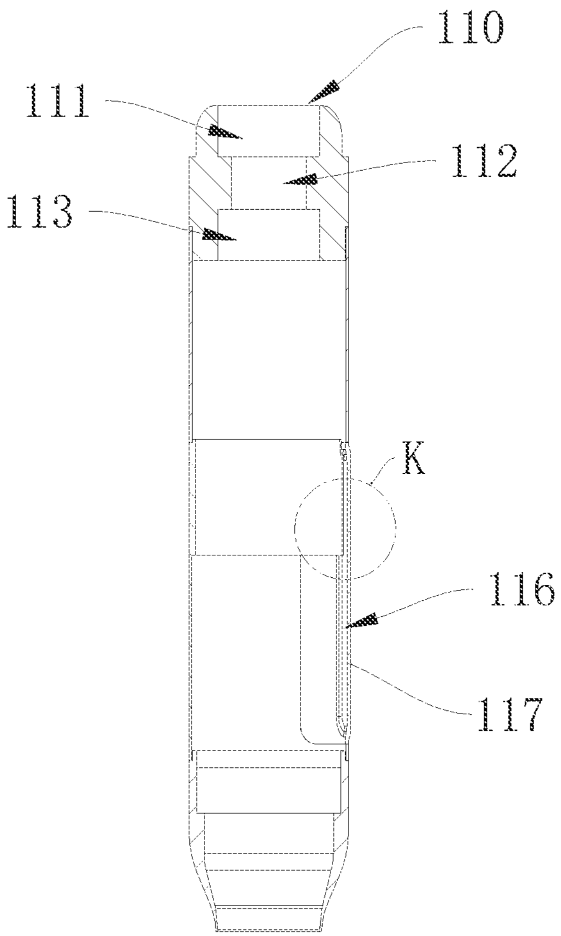
FIG. 15 is a cross-sectional view of the driving housing shown in FIG. 14 taken along the line D-D.
Figure 16:
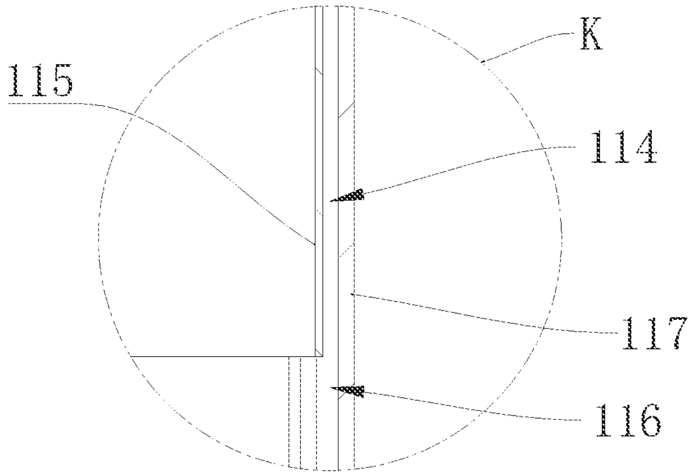
FIG. 16 is a partial enlarged view of the portion K of the driving housing shown in FIG. 15.
Figure 17:
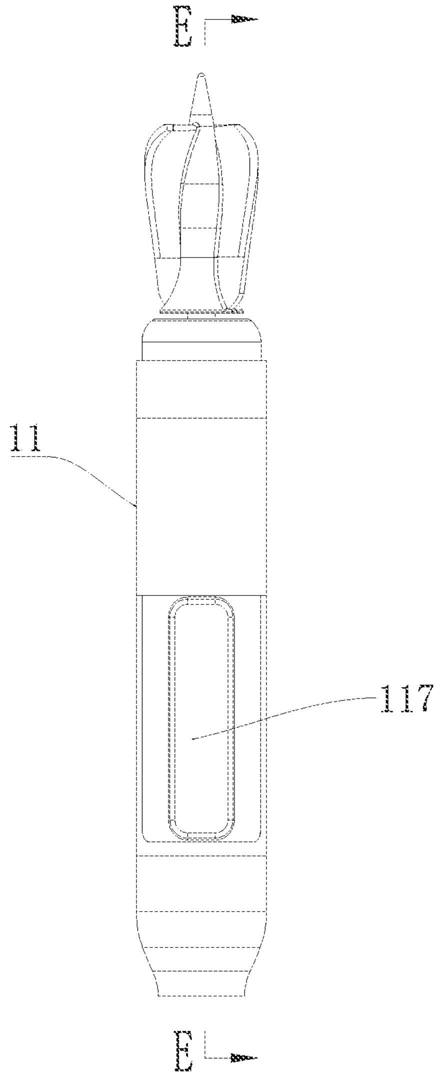
FIG. 17 is a schematic structural view of the blood pump shown in FIG. 1 after removing a cannula assembly and a catheter assembly.
Figure 18:
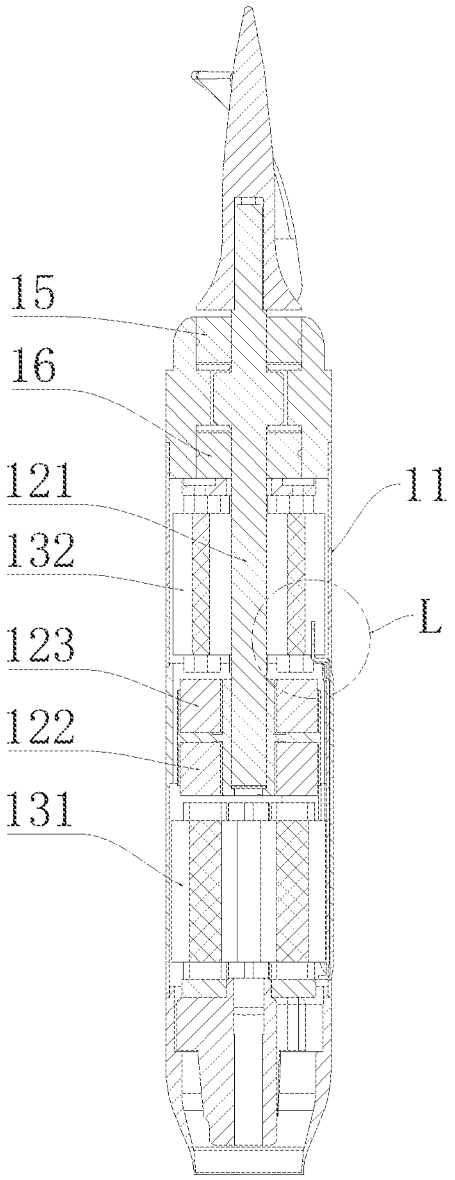
FIG. 18 is a cross-sectional view of the blood pump shown in FIG. 17 taken along the line E-E.
Figure 19:
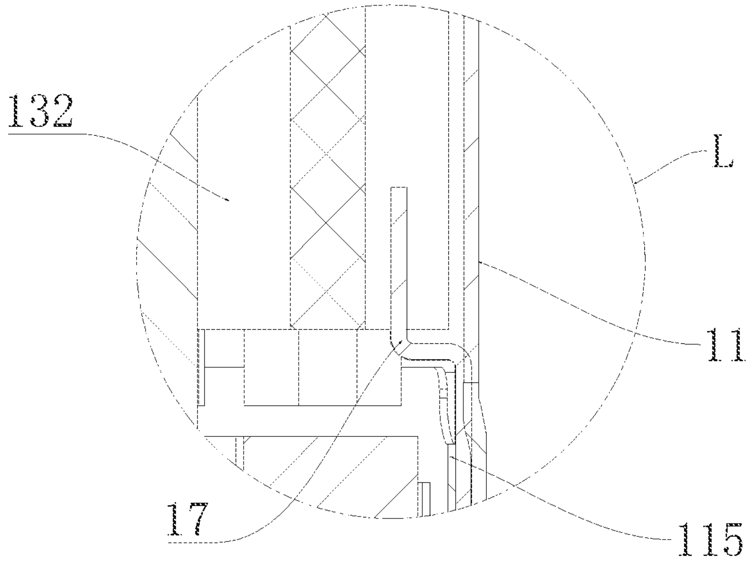
FIG. 19 is a partial enlarged view of the portion L of FIG. 18.
Figure 20:
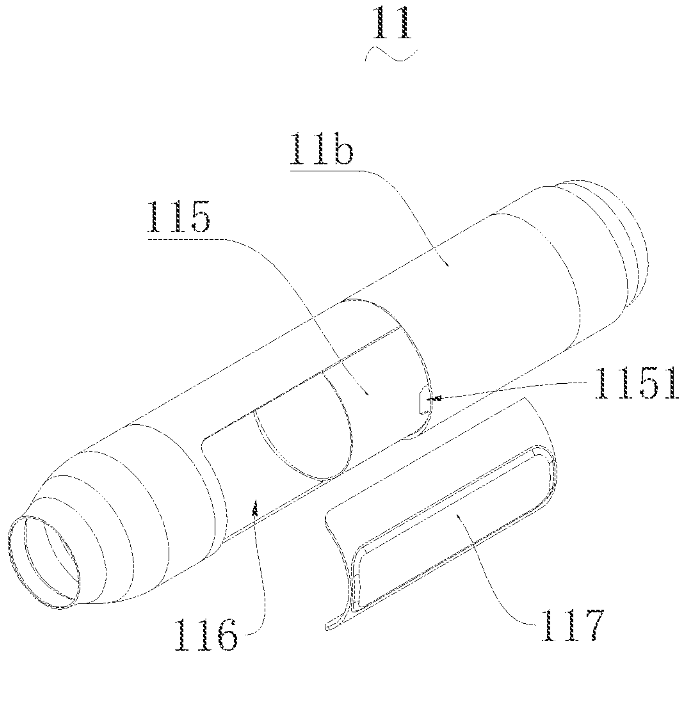
FIG. 20 is an exploded view of the driving housing shown in FIG. 14.

Referring to FIG. 3, FIG. 14, and FIG. 15, specifically, the mounting cavity 11*a* is sequentially provided with a first limiting hole 111, a second limiting hole 112, and a third limiting hole 113 along the axis of the rotating shaft 121. The second limiting hole 112 is in communication with the first limiting hole 111, the third limiting hole 113 is in communication with the second limiting hole 112, and an aperture of the second limiting hole 112 is smaller than an aperture of the first limiting hole 111 and smaller than an aperture of the third limiting hole 113. The first shaft sleeve 15 is accommodated in the first limiting hole 111, the second shaft sleeve 16 is accommodated in the third limiting hole 113, and the limiting ring 125 is accommodated in the second limiting hole 112. By providing the first limiting hole 111, the second limiting hole 112, and the third limiting hole 113, the first shaft sleeve 15 and the second shaft sleeve 16 can be limited in the axial direction of the rotating shaft 121. The mounting opening 110 is an opening on a side of the first limiting hole 111 away from the second limiting hole 112.

In this embodiment, the limiting ring 125 is in clearance fit with a hole wall of the first limiting hole 111.

The cleaning fluid fed from the cleaning pipeline 411 into the driving housing 11 flows through a gap between the second shaft sleeve 16 and the rotating shaft 121, a gap between the limiting ring 125 and the first limiting hole 111, and a gap between the first shaft sleeve 15 and the rotating shaft 121, and enters the cannula assembly 20 from the mounting opening 110, which can not only play a role of backwashing, but also play a role of lubrication between the rotating shaft 121 and the first shaft sleeve 15 and between the rotating shaft 121 and the second shaft sleeve 16.

In this embodiment, a side of the first shaft sleeve 15 adjacent to the limiting ring 125 is provided with a first fluid groove 153, and the first fluid groove 153 is in communication with the gap between the first shaft sleeve 15 and the rotating shaft 121. A side of the second shaft sleeve 16 adjacent to the limiting ring 125 is provided with a second fluid groove 163, and the second fluid groove 163 is in communication with the gap between the second shaft sleeve 16 and the rotating shaft 121. In this way, circulation of the cleaning fluid is facilitated. It should be noted that, in other embodiments, one of the first shaft sleeve 15 and the second shaft sleeve 16 may be provided with a fluid groove, or no fluid groove may be provided.

Referring to FIG. 14 to FIG. 20, the driving housing 11 is further provided with an accommodating cavity 114 separated from the mounting cavity 11*a*. The driving device 10 further includes an electric wire 17. The electric wire 17 is connected to the stator mechanism 13. A portion of the electric wire 17 is located between at least part of the magnetic assembly and the driving housing 11, and the portion of the electric wire 17 located between the magnetic assembly and the driving housing 11 is accommodated in the accommodating cavity 114, so that a cavity wall of the accommodating cavity 114 prevents the electric wire 17 from being in contact with the magnetic assembly. In the illustrated embodiment, the electric wire 17 is electrically connected to the power stator 132. Specifically, the electric wire 17 is electrically connected to the second coil 1323 of the power stator 132. The electric wire 17 are provided between the first magnet 122 and the driving housing 11 and between the second magnet 123 and the driving housing 11, and a portion of the electric wire 17 located between the first magnet 122 and the driving housing 11 and a portion of the electric wire 17 located between the second magnet 123 and the driving housing 11 are both accommodated in the accommodating cavity 114. A position of the magnetic assembly corresponds to a position of the accommodating cavity 114.

The electric wire 17 may be directly electrically connected to the electrical connecting wire in the supply pipeline, or the electric wire 17 is connected to a control unit in the driving device 10, and the control unit is configured to control an operating state of the stator mechanism 13. Specifically, an end of the electric wire 17 is electrically connected to the second coil 1323, and the other end of the electric wire 17 is directly electrically connected to the electrical connecting wire in the supply pipeline or electrically connected to the control unit.

By providing the accommodating cavity 114, the electric wire 17 electrically connected to the stator mechanism 13 is separated from the rotatable magnetic assembly, which can effectively prevent a risk of a malfunction such as breakage or falling off of the electric wire 17 caused by rotation of the electric wire 17 with the magnetic assembly due to contact of the magnetic assembly with the electric wire 17 during the rotation, thereby further ensuring the normal use of the blood pump 100.

Further, a protective member 115 is fixed in the driving housing 11, and the protective member 115 divides an inner cavity of the driving housing 11 into the mounting cavity 11*a* and the accommodating cavity 114. A position of the protective member 115 corresponds to a position of the magnetic assembly. That is, the position of the protective member 115 corresponds to a position of the first magnet 122 and a position of the second magnet 123. The protective member 115 is located between the magnetic assembly and the electric wire 17. The protective member 115 prevents the electric wire 17 from being in contact with the magnetic assembly. That is, the protective member 115 separates the first magnet 122, the second magnet 123, and the flywheel 124 from the accommodating cavity 114.

Specifically, the protective member 115 is provided with a communication hole 1151 in communication with the mounting cavity 11*a* and the accommodating cavity 114 and allowing the electric wire 17 to extend through, so as to enable the electric wire 17 to extend through the communication hole 1151 to be electrically connected to the stator mechanism 13 in the mounting cavity 11*a*.

In order to facilitate the mounting of the electric wire 17 connecting the driving stator 131 and the power stator 132, the driving housing 11 includes a shell body 11*b* and a sealing cover 117. The shell body 11*b* is further provided with a mounting opening 116, and the sealing cover 117 sealingly covers on the mounting opening 116. The protective member 115 shields part of the mounting opening 116, and at least part of the accommodating cavity 114 is jointly defined by the sealing cover 117 and the protective member 115. At least a portion of the accommodating cavity 114 is formed by the sealing cover 117 and the protective member 115.

Figure 21:
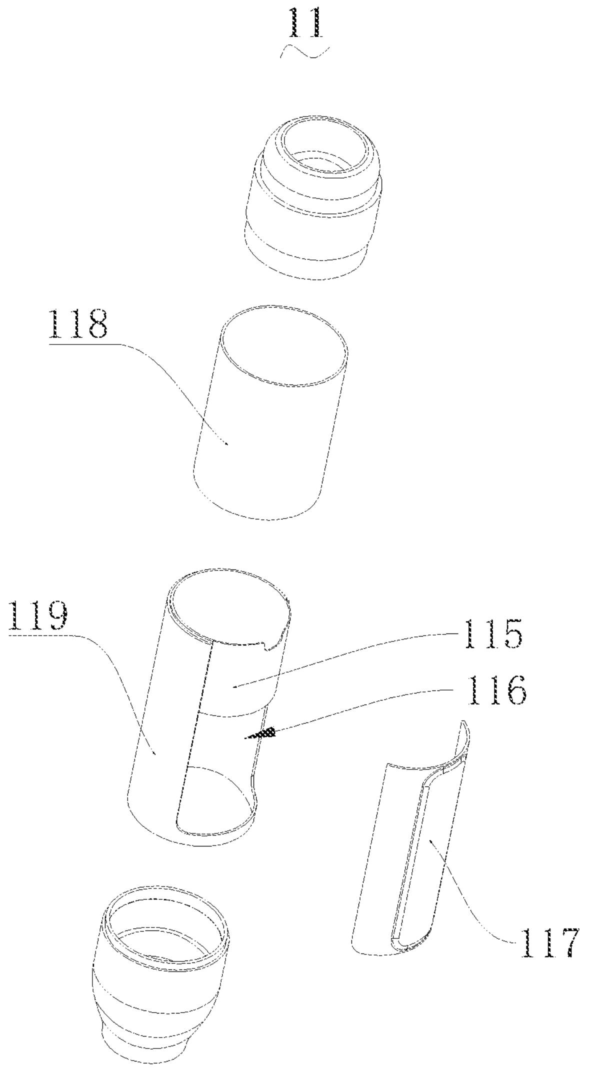
FIG. 21 is another exploded view of the driving housing shown in FIG. 20.

Referring to FIG. 21, the driving housing 11 includes a first housing 118 and a second housing 119 docked with the first housing 118, and the protective member 115 is located on the second housing 119. The driving housing 11 is designed as a combination of a plurality of housings, which can facilitate assembly of internal parts of the driving device 10.

In some embodiments, the accommodating cavity 114 is formed in a manner of, but not limited to, providing the protective member 115. In some embodiments, the accommodating cavity 114 may alternatively be a channel directly provided on a side wall of the driving housing 11 and used for allowing the electric wire 17 to extend through.

It should be noted that the driving device 10 is not limited to the above structure. In some embodiments, the driving device 10 has two flywheels, and the two flywheels are both provided between the power stator 132 and the driving stator 131. The two flywheels are both fixedly connected to the rotating shaft 121 and arranged along the axis of the rotating shaft 121, and the first magnet 122 and the second magnet 123 are mounted on the two flywheels, respectively. In this case, the position of the accommodating cavity 114 corresponds to the first magnet 122 and the second magnet 123, and the protective members 115 are arranged between the flywheel on which the first magnet 122 is mounted and the electric wire 17 and between the flywheel on which the second magnet 123 is mounted and the electric wire 17. It should be understood that, in this case, the rotor 12 may be provided with no flywheel. In this case, the protective members 115 are provided between the first magnet 122 and the electric wire 17 and between the second magnet 123 and the electric wire 17. Alternatively, one flywheel is provided, and the flywheel is configured to mount one of the first magnet 122 and the second magnet 123.

Alternatively, the power stator 132 is located between two flywheels. That is, one flywheel is located between the impeller 30 and the power stator 132, and the other flywheel is located between the power stator 132 and the driving stator 131. The first magnet 122 is fixed to the flywheel between the power stator 132 and the driving stator 131, and the second magnet 123 is fixed to the flywheel between the impeller 30 and the power stator 132. That is, the first magnet 122 is located between the power stator 132 and the driving stator 131, and the second magnet 123 is located between the impeller 30 and the power stator 132. In this case, the electric wire 17 exists between the first magnet 122 and the driving housing 11. In order to prevent the electric wire 17 from being in contact with the first magnet 122 or the flywheel on which the first magnet 122 is mounted, the portion of the electric wire 17 located between the first magnet 122 and the driving housing 11 is accommodated in the accommodating cavity 114. Correspondingly, the protective member 115 is located between the flywheel on which the first magnet 122 is mounted and the electric wire 17. It should be understood that, in this case, the rotor 12 may be provided with no flywheel. In this case, the protective member 115 is located between the first magnet 122 and the electric wire 17.

Alternatively, in some embodiments, the rotating shaft 121 may be provided to pass through the driving stator 131, and the rotating shaft 121 extends through the driving stator 131 and the power stator 132. In this case, the entire magnetic assembly may be provided between the driving stator 131 and the power stator 132. In this case, the arrangement of the accommodating cavity may be similar to that shown in FIG. 18 to FIG. 21. Alternatively, the power stator 132 is located between the first magnet 122 and the second magnet 123, alternatively, the driving stator 131 and the power stator 132 are both located between the first magnet 122 and the second magnet 123. In this case, the electric wire 17 exists between the first magnet 122 and the driving housing 11. In order to prevent the electric wire 17 from being in contact with the first magnet 122 or the flywheel on which the first magnet 122 is mounted, the portion of the electric wire 17 located between the first magnet 122 and the driving housing 11 is accommodated in the accommodating cavity 114. Correspondingly, the protective member 115 is located between the flywheel on which the first magnet 122 is mounted and the electric wire 17. It should be understood that, in this case, the rotor 12 may be provided with no flywheel. In this case, the protective member 115 is located between the first magnet 122 and the electric wire 17.

Alternatively, in some embodiments, the driving device 10 is provided only with the power stator 132. The power stator 132 can generate a rotating magnetic field for driving the magnetic assembly to rotate. The electric wire 17 is electrically connected to the power stator 132, the rotating shaft 121 rotatably extends through the power stator 132, and the magnetic assembly is closer to an end portion of an end of the rotating shaft 121 accommodated in the mounting cavity 11*a* than the power stator 132. In this case, the magnetic assembly has at least a magnet corresponding to the power stator 132, and the power stator 132 can generate a rotating magnetic field for driving the magnet to rotate.

The foregoing embodiments are merely intended to describe the technical solutions of the present disclosure, but not to limit the present disclosure. Although the present disclosure is described in detail with reference to the foregoing embodiments, those of ordinary skill in the art should understand that they may still make modifications to the technical solutions described in the foregoing embodiments or make equivalent replacements to some technical features thereof. However, such modifications or replacement do not cause the essence of the corresponding technical solutions to depart from the spirit and scope of the technical solutions of the embodiments of the present disclosure, and should be included within the protection scope of the present disclosure.

What is claimed is:

1. A driving device, comprising:

a driving housing provided with a mounting cavity and an accommodating cavity separated from the mounting cavity;

a rotor comprising a rotating shaft and a magnetic assembly, an end of the rotating shaft being accommodated in the mounting cavity, the rotating shaft being capable of rotating relative to the driving housing, and the magnetic assembly being fixedly connected to the rotating shaft;

a stator mechanism accommodated in the mounting cavity, the stator mechanism being capable of generating a rotating magnetic field that drives the magnetic assembly to rotate, and the magnetic assembly being capable of driving the rotating shaft to rotate around an axis of the rotating shaft; and an electric wire electrically connected to the stator mechanism, a portion of the electrical wire being located between at least part of the magnetic assembly and the driving housing, and the portion of the electric wire located between the magnetic assembly and the driving housing being accommodated in the accommodating cavity, so that a cavity wall of the accommodating cavity prevents the electric wire from being in contact with the magnetic assembly, wherein a protective member is fixed in the driving housing, the protective member divides an inner cavity of the driving housing into the mounting cavity and the accommodating cavity, the protective member is located between the electric wire and at least part of the magnetic assembly, and the protective member prevents the electric wire from being in contact with the magnetic assembly, and wherein the driving housing comprises a first housing and a second housing docked with the first housing, the first housing and the second housing cooperatively define the mounting cavity, and the protective member is located on the second housing.

2. The driving device according to claim 1, wherein the stator mechanism comprises a power stator, the power stator is capable of generating the rotating magnetic field that drives the magnetic assembly to rotate, the electric wire is electrically connected to the power stator, the rotating shaft is capable of rotatably extending through the power stator, and the magnetic assembly is closer to an end portion of an end of the rotating shaft accommodated in the mounting cavity than the power stator.

3. The driving device according to claim 1, wherein the magnetic assembly comprises a first magnet and a second magnet, both the first magnet and the second magnet is fixedly connected to the rotating shaft, and the stator mechanism comprises a driving stator and a power stator, the driving stator and the power stator are arranged along the axis of the rotating shaft, the driving stator is capable of generating a rotating magnetic field that drives the first magnet to rotate, the power stator is capable of generating a rotating magnetic field that drives the second magnet to rotate; wherein the first magnet is located between the driving stator and the power stator, a portion of the electric wire is located between the first magnet and the driving housing, and the portion of the electric wire located between the first magnet and the driving housing is accommodated in the accommodating cavity.

4. The driving device according to claim 3, wherein the second magnet is located between the power stator and the first magnet, the electric wire is provided between the first magnet and the driving housing, and between the second magnet and the driving housing, and a portion of the electric wire located between the first magnet and the driving housing and a portion located between the second magnet and the driving housing are both accommodated in the accommodating cavity.

5. The driving device according to claim 3, wherein the magnetic assembly further comprises a flywheel fixedly connected to the rotating shaft, the flywheel is located between the driving stator and the power stator, and both the first magnet and the second magnet are mounted on the flywheel.

6. The driving device according to claim 5, wherein the flywheel comprises a disc-shaped portion fixedly sleeved on the rotating shaft, the first magnet and the second magnet are provided on two opposite sides of the disc-shaped portion, respectively, both the first magnet and the second magnet are annular Halbach array magnets, the first magnet comprises a plurality of first magnetic blocks whose magnetization directions are parallel to an axis of the first magnet, and the second magnet comprises a plurality of second magnetic blocks whose magnetization directions are parallel to an axis of the second magnet, the plurality of second magnetic blocks and the plurality of first magnetic blocks are provided on the two opposite sides of the disc-shaped portion around the rotating shaft, respectively, and in an extension direction of the rotating shaft, each of the second magnetic blocks is provided opposite to one of the first magnetic blocks, and polarities of the first magnetic block and the second magnetic block arranged oppositely on a side thereof facing the disc-shaped portion are opposite.

7. The driving device according to claim 5, wherein the flywheel comprises a disc-shaped portion and a tubular portion, the tubular portion fixedly extends through a middle portion of the disc-shaped portion and is coaxial with the disc-shaped portion, the rotating shaft is fixedly connected to the tubular portion, and the first magnet and the second magnet are provided on two opposite sides of the disc-shaped portion, respectively.

8. The driving device according to claim 7, wherein the flywheel further comprises an outer ring wall surrounding the disc-shaped portion, the outer ring wall, the tubular portion, and the disc-shaped portion cooperatively define a first accommodating portion and a second accommodating portion configured to accommodate the first magnet and the second magnet, respectively, and the first accommodating portion and the second accommodating portion are separated by the disc-shaped portion.

9. The driving device according to claim 8, wherein, in an axial direction of the tubular portion, a side of the first magnet away from the disc-shaped portion is higher than the outer ring wall by a distance; and a side of the second magnet away from the disc-shaped portion is higher than the outer ring wall by a distance.

10. The driving device according to claim 3, wherein the driving stator comprises a plurality of first magnetic cores and first coils provided spaced apart for one circle around the axis of the rotating shaft, and the power stator comprises a plurality of second magnetic cores and second coils provided spaced apart for one circle around the axis of the rotating shaft, both the first magnetic cores and the second magnetic cores comprises magnetic posts, the first coils are wound around the magnetic posts of the first magnetic cores, the second coils are wound around the magnetic posts of the second magnetic cores, and cross-sectional areas of the magnetic posts of the first magnetic cores are greater than cross-sectional areas of the magnetic posts of the second magnetic cores.

11. The driving device according to claim 10, wherein the magnetic posts of the first magnetic cores and the magnetic posts of the second magnetic cores are all in a shape of a triangular prism, and edges of each of the magnetic posts are rounded.

12. The driving device according to claim 3, wherein the rotating shaft rotatably extending through the power stator, and the driving stator and the rotating shaft are provided spaced apart along the axis of the rotating shaft.

13. The driving device according to claim 1, wherein the protective member is provided with a communication hole in communication with the mounting cavity and the accommodating cavity and allowing the electric wire to extend through, so as to allow the electric wire to extend through the communication hole to be electrically connected to the stator mechanism in the mounting cavity.

14. The driving device according to claim 1, wherein the driving housing comprises a shell body and a sealing cover, the shell body is further provided with a mounting opening, the mounting opening is in communication with the mounting cavity, the sealing cover sealingly covers on the mounting opening, and at least a portion of the accommodating cavity is formed by the sealing cover and the protective member.

15. The driving device according to claim 1, wherein the driving device further comprises a first shaft sleeve and a second shaft sleeve, both the first shaft sleeve and the second shaft sleeve are accommodated in the mounting cavity and are fixedly connected to the driving housing, the rotating shaft rotatably extends through the first shaft sleeve and the second shaft sleeve, and the rotor further comprises a limiting ring, the limiting ring is fixedly sleeved on the rotating shaft, the limiting ring is located between the first shaft sleeve and the second shaft sleeve, and an outer diameter of the limiting ring is greater than an inner diameter of the first shaft sleeve and an inner diameter of the second shaft sleeve, respectively, so as to limit the rotating shaft in an extension direction of the rotating shaft.

16. The driving device according to claim 15, wherein the mounting cavity is provided with a first limiting hole, a second limiting hole, and a third limiting hole provided along the extension direction of the rotating shaft, the second limiting hole is in communication with the first limiting hole, the third limiting hole is in communication with the second limiting hole, an aperture of the second limiting hole is smaller than an aperture of the first limiting hole and smaller than an aperture of the third limiting hole, the first shaft sleeve is accommodated in the first limiting hole, the second shaft sleeve is accommodated in the third limiting hole, and the limiting ring is accommodated in the second limiting hole.

17. The driving device according to claim 1, wherein the driving housing is further provided with a mounting opening in communication with the mounting cavity, an end of the rotating shaft extends from the mounting opening to the outside of the driving housing, the driving device further comprises a shaft sleeve fixedly connected to the driving housing, the shaft sleeve is provided at the mounting opening, and the rotating shaft rotatably extends through the shaft sleeve, wherein a gap between the shaft sleeve and the rotating shaft is less than or equal to 2 μm.

18. A blood pump, comprising:

the driving device according to claim 1; and an impeller fixedly connected to the rotating shaft, the impeller being capable of rotating along with the rotating shaft.

* * * * *